United States Patent [19]

Takatori et al.

[11] Plant 4,675

[45] Mar. 24, 1981

[54] ASPARAGUS PLANT

[75] Inventors: Frank H. Takatori; Franklin D. Souther, both of Riverside, Calif.

[73] Assignee: The Regents of the University of California, Berkeley, Calif.

[21] Appl. No.: 105,171

[22] Filed: Dec. 19, 1979

[51] Int. Cl.[3] ..... A01H 5/00

[52] U.S. Cl. ..... Plt./89

[58] Field of Search ..... Plt./89

*Primary Examiner*—James R. Feyrer

*Attorney, Agent, or Firm*—Townsend and Townsend

[57] ABSTRACT

A new and distinct variety of male asparagus plant primarily characterized by its high lateral branching at or above the 16th node (about 17.5 inches above the soil level), its vigorous growth and production of between 25 to 35 canes per season which grow to a height between six and eight feet at plant maturity and further characterized by its ability to produce fast growing spears with tight heads and which are straight, round, and smooth.

2 Drawing Figures

DESCRIPTION

This invention relates to a new and distinct male clone of asparagus designated as M-120. Plant M-120 was selected from a plot of variety U.C. 309, which was planted at the University of California Agricultural Experiment Station, Riverside, Calif., in 1963. The source of seed for the U.C. 309 planting was obtained from Mr. J. Hanna, formerly a member of the Department of Vegetable Crops, University of California, Davis, Calif.

Male plant M-120 is a vigorous growing, multi-caned plant. A well established M-120 plant, three years or older in age, will produce between 25 and 35 canes per season. The diameter of the canes measured at soil level will range between ¾ and 1 inch in diameter.

Plant growth is erect and the foliage, referred to as fern, will exceed six feet in height with lateral branches extending about three feet in all directions. The foliage and canes are Dark Green (Plate XVIII) in color. The first lateral branching occurs about 17.5 inches above the soil level and exhibits a plant characteristic referred to as "high branching." This characteristic is a particularly distinguishing one from other known varieties of asparagus plant.

Asparagus is a dioecious plant, individual plants being either male or female in sex.

In the accompanying drawing.

Figure 1:
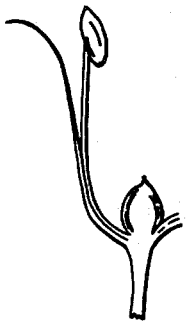
FIG. 1 shows typical male parts of M-120.
Figure 2:
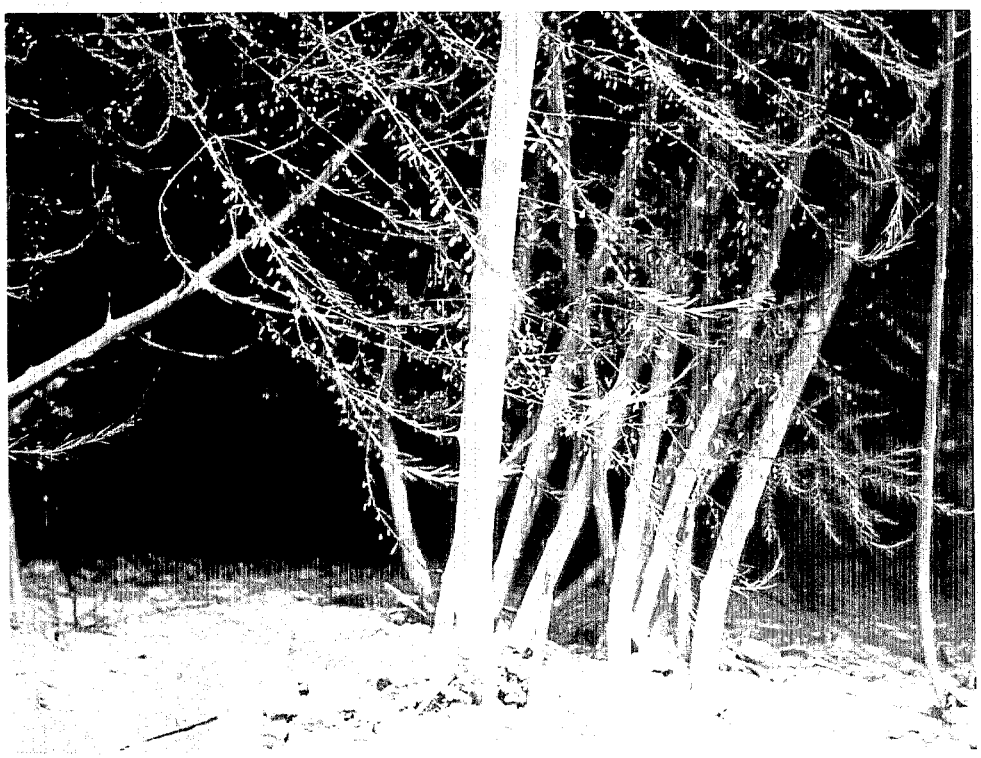
FIG. 2 shows the "high branching" characteristic of M-120 and the numerous canes per plant developed in one season.

The only existing methods of asexual reproduction of asparagus plants for the multiplication of plants of this invention are crown division or tissue culture. The plant of this invention has been asexually reproduced by tissue culture techniques which are more conducive to large scale multiplication of asparagus plants than is crown division.

The colors designated hereinafter are approximate and may vary with several factors including soil type, nutrition, temperature and maturity. The colors have been determined by comparison to the colors in "Color Standards and Color Nomenclature" by Robert Ridgway, Washington, D.C., 1912.

PLANT CHARACTERISTICS

Spear: Emerges early in the spring, fast growing, straight, round, smooth with slow taper. Heads are very tight, smooth and initiate lateral branches at or above the 16th node when the spears are 11 to 12 inches in height. Spear color is Biscay Green (Plate XVII). The spear bract is Lumiere Green (Plate XVII).

Foliage: An erect Dark Green (Plate XVIII) perennial herb with straight, smooth stems, having many lateral branches. A plant three years or older initiates between 25 and 35 stems that grow to a height between six and eight feet. The average spear diameter at soil level is between ¾ and 1 inch. The mature fern is Cedar Green (Plate VI).

The first lateral branch is initiated at or above the 16th node in the spring when the spear is 11 to 12 inches in height and at maturity when the cane is 17.5 inches in height. The mature cane is Grass Green (Plate VI) and the cane bract is Ochraceous-Buff (Plate XV).

Inflorescence: One to four, usually two in axils with cladodes. Flowers Yellow-Green (Plate VI), campanulate, stamens 6 and 0.60 to 0.65 cm. in length. The color of the flower is Pale Virdine Yellow (Plate V).

Fruit: None.

Crown-root: Crown a woody rhizome, with long, fleshy storage roots and fibrous absorptive roots. Fleshy storage roots ¼ to ⅜ inch in diameter and many feet in length.

We claim:

1. The new and distinct variety of asparagus plant herein described and illustrated and identified by the characteristics enumerated above.

* * * * *